(12) United States Patent
Lecke

(10) Patent No.: US 12,357,735 B2
(45) Date of Patent: Jul. 15, 2025

(54) SYSTEM FOR DETECTING BLOOD IN A DIALYSATE FLOW OF A DIALYSIS MACHINE

(71) Applicant: B. Braun Avitum AG, Melsungen (DE)

(72) Inventor: Tobias Lecke, Bebra (DE)

(73) Assignee: B. Braun Avitum AG, Melsungen (DE)

( * ) Notice: Subject to any disclaimer, the term of this patent is extended or adjusted under 35 U.S.C. 154(b) by 531 days.

(21) Appl. No.: 17/913,139

(22) PCT Filed: Mar. 12, 2021

(86) PCT No.: PCT/EP2021/056307
§ 371 (c)(1),
(2) Date: Sep. 20, 2022

(87) PCT Pub. No.: WO2021/190954
PCT Pub. Date: Sep. 30, 2021

(65) Prior Publication Data
US 2023/0135616 A1  May 4, 2023

(30) Foreign Application Priority Data
Mar. 23, 2020  (DE) ...................... 10 2020 203 674.8

(51) Int. Cl.
*A61M 1/16* (2006.01)
(52) U.S. Cl.
CPC ... *A61M 1/1609* (2014.02); *A61M 2205/3313* (2013.01)

(58) Field of Classification Search
CPC .. A61M 2205/3313; A61M 2205/3306; A61M 2205/15; A61M 2205/705; A61M 1/3656
See application file for complete search history.

(56) References Cited

U.S. PATENT DOCUMENTS

| | | | |
|---|---|---|---|
| 4,017,190 A | 4/1977 | Fischel | |
| 4,181,610 A | 1/1980 | Shintani et al. | |
| 6,666,840 B1 | 12/2003 | Falkvall et al. | |
| 2003/0147770 A1* | 8/2003 | Brown | A61M 1/3681 422/38 |
| 2005/0051466 A1* | 3/2005 | Carter | G01N 15/05 210/512.1 |

(Continued)

FOREIGN PATENT DOCUMENTS

| | | |
|---|---|---|
| CN | 102387739 A | 3/2012 |
| CN | 103533972 A | 1/2014 |

(Continued)

OTHER PUBLICATIONS

Office Action received in Japanese Application No. 2022-557976 dated Apr. 25, 2023, with translation, 3 pages.

(Continued)

*Primary Examiner* — Rebecca E Eisenberg
*Assistant Examiner* — Matthew Wrubleski
(74) *Attorney, Agent, or Firm* — Christopher A. Rothe; CM Law

(57) ABSTRACT

A method and a detection device for detecting blood in a dialysate flow of a dialysis machine during extracorporeal blood treatment.

14 Claims, 5 Drawing Sheets

(56) References Cited

U.S. PATENT DOCUMENTS

| | | | |
|---|---|---|---|
| 2009/0262351 A1* | 10/2009 | Erickson | A61M 5/1684 |
| | | | 356/409 |
| 2013/0033697 A1* | 2/2013 | Zhang | G01N 33/49 |
| | | | 356/39 |
| 2013/0153474 A1 | 6/2013 | Frorip et al. | |
| 2016/0058933 A1 | 3/2016 | Ballantyne et al. | |

FOREIGN PATENT DOCUMENTS

| | | |
|---|---|---|
| DE | 102011008482 A1 | 1/2012 |
| JP | 2002516722 A | 6/2002 |
| WO | 2011154514 A1 | 12/2011 |

OTHER PUBLICATIONS

Search Report received in International Application No. PCT/EP2021/056307 dated Jun. 22, 2021, with translation, 7 pages.
Written Opinion received in International Application No. PCT/EP2021/056307 dated Jun. 22, 2021, with translation, 13 pages.

* cited by examiner

SYSTEM FOR DETECTING BLOOD IN A DIALYSATE FLOW OF A DIALYSIS MACHINE

CROSS-REFERENCE TO RELATED APPLICATIONS

This application is the United States national stage entry of International Application No. PCT/EP2021/056307, filed Mar. 12, 2021, and claims priority to German Application No. 10 2020 203 674.8, filed Mar. 23, 2020. The contents of International Application No. PCT/EP2021/056307 and German Application No. 10 2020 203 674.8 are incorporated by reference herein in their entireties.

FIELD

The invention relates to a detection device and a method for detecting blood in a dialysate flow of a dialysis machine during an extracorporeal blood treatment.

BACKGROUND

Dialysis machines provided for extracorporeal blood treatment comprise a dialyzer with a blood chamber and a dialysate chamber, which are separated from one another by means of a semipermeable membrane. During the blood treatment, blood is conveyed through the blood chamber in an extracorporeal blood circuit. At the same time, a dialysate, which may also be referred to as a dialysis fluid, flows through the dialysate chamber. If the semipermeable membrane ruptures due to failure, blood from the extracorporeal blood circuit can enter the dialysate flow. Such blood leakage can lead to serious medical impairments of the patient to be treated, and to technical faults in the dialysis machine. It is for this reason that dialysis machines are usually provided with a detection device, by means of which blood in the dialysate flow can be detected.

Such a detection device is known from U.S. Pat. No. 4,181,610 B1. The known detection device comprises a first light source and a second light source which are arranged together on a first side of a light-transmissive fluid-guiding channel that serves to guide the fluid of the dialysate flow, and which emit light at different wavelengths. Moreover, the known detection device comprises a control device which is configured to alternately control the two light sources such that the light thereof is alternately radiated into the dialysate flow. A single detector is arranged on an opposite side of the fluid-guiding channel, and is configured to register the light components of the two light sources transmitted through the dialysate flow and to produce corresponding signals. In this case, a first signal represents the intensity of the registered transmitted light component of the first light source. A second signal represents the intensity of the registered transmitted light component of the second light source. In the case of blood leakage, the light radiated in by the first light source is absorbed to a greater extent on account of its wavelength than the light radiated in by the second light source. As a result, the blood leakage can be detected by a comparison between the first signal and the second signal. Further, the known detection device comprises a calibration device that is configured to calibrate the brightness levels of the two light sources. This is intended to avoid brightness variations between the two light sources due to operational reasons being incorrectly interpreted as blood leakage.

SUMMARY

It is an object of the invention to provide a detection device and a method of the type set forth at the outset, which have a simplified structure or a simplified implementation in relation to the prior art and which at the same time facilitate reliable detection of blood in the dialysate flow.

The method according to the invention comprises the steps of: a) radiating light into the dialysate flow; b) registering, at a first detection location, a light component of the light radiated in that has been transmitted through the dialysate flow and producing a first signal which represents the intensity of the registered transmitted light component; c) registering, at a second detection location, a light component of the light radiated in that has been scattered in the dialysate flow and producing a second signal which represents the intensity of the registered scattered light component; d) producing a detection signal on the basis of the first signal produced and the second signal produced. The solution according to the invention allows a complicated calibration of the brightness of the radiated-in light to be dispensed with. This is because possible intensity variations of the radiated-in light have the same effect on the transmitted light component as they do on the scattered light component. Accordingly, the first signal and the second signal have the same positive or the same negative change in the case of intensity variations of the radiated-in light. By contrast, the intensity of the transmitted light component reduces with increasing blood concentration in the dialysate flow and the intensity of the scattered light component increases at the same time. Accordingly, the first signal and the second signal change in the opposite sense in the case of blood leakage—unlike in the case of the brightness variation of the radiated-in light. This can be taken into account when producing the detection signal on the basis of the first signal and the second signal. As a result, the method according to the invention facilitates a simple but nevertheless reliable detection of blood in the dialysate flow since incorrect detections on account of brightness variations of the radiated-in light can be avoided, while at the same time dispensing with a calibration in this respect.

Step a) comprises radiating light into the dialysate flow. In this context, the inventors have recognized that radiating in light that is visible to humans is particularly advantageous. In this respect, it is possible for example to radiate in red, green or blue light, with "red" and "blue" representing the boundaries of the visible spectrum. This is because this can avoid an impairment of the detection by substances usually eliminated with urine that are situated in the dialysate flow. Further, it was recognized that radiating in blue light offers advantages with regard to a particularly sensitive registration of the light, in particular in step c). The light is preferably radiated in in a radiated-in direction oriented transversely, preferably perpendicularly, to a flow direction of the dialysate flow. The light can be radiated in continuously over time and/or at discrete time intervals.

Step b) comprises registering the light component of the light radiated in that has been transmitted through the dialysate flow. The intensity of the registered transmitted light component reduces in the case of blood leakage. This is due to absorption, reflection and/or scattering effects at the blood particles of the blood that has seeped in. The "summation" of absorption, scattering and further effects that reduce the intensity of the light can also be referred to as attenuation. Step b) moreover comprises producing the first signal. Since the first signal represents the intensity of the registered transmitted light component, the first signal, in particular the value thereof, changes accordingly in the case of blood leakage. Preferably, the first signal reduces in the case of blood leakage. Expressed differently, the value of the first signal reduces over time in the case of blood leakage.

Expressed yet again differently, a change in the first signal over time is preferably negative in the case of blood leakage. The first signal can be produced at discrete time intervals and/or continuously over time.

Step c) comprises registering the light component of the light radiated in that has been scattered in the dialysate flow. The concentration of light-scattering blood particles in the dialysate flow increases in the case of blood leakage. Accordingly, the intensity of the scattered light component increases in the case of blood leakage. Step c) moreover comprises producing the second signal. Since the second signal represents the intensity of the registered scattered light component, the second signal, in particular the value thereof, changes accordingly. Preferably, the second signal increases in the case of blood leakage. Expressed differently, a change in the second signal over time is preferably positive in the case of blood leakage. The second signal can be produced continuously over time and/or at discrete time intervals.

Step d) comprises producing the detection signal. In particular, the detection signal can be a signal for controlling at least one function of a detection device for carrying out the method, at least one function of the dialysis machine and/or a signal that is perceivable by a user of the method, in particular an acoustic and/or optical signal. The detection signal is produced on the basis of the first signal produced and the second signal produced. In this case, it is possible in particular to evaluate a value, an arithmetic sign, an absolute value, a change over time, a rate of change over time or the like of the respective signal.

In an embodiment of the invention, the detection signal is produced when a change in the first signal over time is in the opposite sense to a change in the second signal over time. Accordingly, the detection signal is produced when the first signal, in particular the value thereof, decreases over time and, at the same time, the second signal, in particular the value thereof, increases over time, or vice versa. This is a particularly advantageous embodiment of the invention.

In a further embodiment of the invention, the method comprises the steps of: e) emitting UV light, with the UV light being radiated into the dialysate flow and being radiated past the dialysate flow; f) registering, at the first detection location, a UV light component of the UV light radiated in that has been transmitted through the dialysate flow and producing a third signal which represents the intensity of the registered transmitted UV light component; g) registering, at the second detection location, the UV light radiated past the dialysate flow and producing a fourth signal which represents the intensity of the registered UV light radiated past said dialysate flow; h) determining a Kt/V value on the basis of the third signal produced and the fourth signal produced. This is a particularly preferred embodiment of the invention. This is because this embodiment facilitates an additional determination of what is known as the Kt/V value with a registration "at the same location" of the UV light intensities required to this end. The term "Kt/V value", or abbreviated "Kt-V", is known as such in the field of medical engineering. The Kt/V value is related to a urea concentration in the dialysate flow. If a relative change in the urea concentration is known, the Kt/V value can be determined on the basis of known chemical and/or physical relationships. The change in the urea concentration is related to a change in the third signal produced. Expressed differently: the urea concentration in the dialysate flow is a marker for the progress of the extracorporeal blood treatment; the lower the concentration in the dialysate flow, the lower the concentration in the blood of the patient to be treated; a relative measurement of this concentration allows determination of the Kt/V value. As a result, it is known that the Kt/V value allows conclusions to be drawn about the progress of the extracorporeal blood treatment and hence, in particular, about a required duration of treatment. The intensities of the UV light required to determine the Kt/V value are registered at the first detection location and at the second detection location, and hence are registered at the detection locations for the blood leakage detection. This facilitates a significant simplification of the implementation of the method and, at the same time, facilitates a significant simplification in the structure of a detection device configured to implement the method. Against this background, this embodiment of the invention consequently relates to a method for detecting blood and a toxin, in particular urea, in a dialysate flow of a dialysis machine during an extracorporeal blood treatment. Since the method according to this embodiment of the invention is provided for detecting both blood and the toxin, it is also possible to refer to a "combined detection".

Step e) comprises emitting UV light. The emitted UV light is radiated into the dialysis flow and past same. The UV light is preferably radiated into the dialysate flow in a radiated-in direction that is oriented transversely, preferably perpendicularly, to the flow direction of the dialysate flow. Further preferably, the UV light and the light—to be radiated in according to step a)—are radiated into the dialysate flow in a common plane. The UV light can be emitted, radiated in and/or radiated past continuously over time and/or at discrete time intervals. Preferably, the UV light is radiated past the dialysis flow in an emission direction oriented transversely, preferably perpendicularly, to the flow direction of the dialysate flow.

Step f) comprises registering the light component of the UV light radiated in that has been transmitted through the dialysate flow. The intensity of the transmitted UV light component reduces with increasing urea concentration. This is due to absorption, reflection and/or scattering effects. Step f) moreover comprises producing the third signal. Since the latter represents the intensity of the registered transmitted UV light component, the third signal, in particular the value thereof, reduces with increasing urea concentration in the dialysate flow. The third signal can be produced continuously over time and/or at discrete time intervals. The transmitted UV light component is registered at the first detection location, and hence registered at the location where the transmitted light component of the light radiated in for the purposes of the blood detection is already registered.

Step g) comprises registering the UV light that has been radiated past the dialysate flow. The UV light is emitted directly, or optionally after one or more deflections, in the direction of the second detection location and is registered there—just like the scattered light component of the light radiated in for the purposes of detecting blood. Step g) moreover comprises producing the fourth signal. The fourth signal represents the intensity of registered UV light that has been radiated past said dialysate flow and acts as a reference signal for the third signal. This is because the intensity of the UV light that has been radiated past said dialysate flow is independent of the urea concentration. Consequently, it is possible to identify possible variations in the brightness of the emitted UV light as such during an evaluation of the third and the fourth signal. The fourth signal can be produced continuously over time and/or at discrete time intervals.

Step h) comprises determining the Kt/V value. The determination is carried out on the basis of the third signal produced and the fourth signal produced. In this case, the fourth signal acts as a reference signal. The third signal represents the intensity of the registered transmitted UV light component, which in turn is related to the UV light absorption. It is known that there is an almost linear relationship between the UV light absorption and the urea concentration in the dialysate flow, and so the Kt/V value is determined on the basis of relationships known as a matter of principle.

In a further embodiment of the invention, the second detection location is shielded from the UV light radiated into the dialysate flow. This avoids the UV light radiated into the dialysate flow being steered in the direction of the second detection location directly, after reflection or due to any other optical effects, and falsifying the registration of the UV light radiated past said dialysate flow, and hence the production of the fourth signal, there in an unwanted manner.

In a further embodiment of the invention, the light and the UV light are radiated into the dialysate flow in alternating fashion, preferably with an alternation frequency of 1 kHz, with the first signal and the third signal being produced alternately by means of a first detector arranged at the first detection location and with the second signal and the fourth signal being produced alternately by means of a second detector arranged at the second detection location. This is a particularly preferred embodiment of the invention. A quasi-simultaneous blood leakage detection and Kt/V value determination is possible in the case of a sufficiently high alternation frequency.

The detection device according to the invention is configured to carry out the above-described method and comprises: at least one light source configured to radiate light into the dialysate flow; a first detector arranged at a first detection location, with the first detector being configured to register a light component of the light radiated in that has been transmitted through the dialysate flow and to produce a first signal which represents the intensity of the registered transmitted light component; a second detector arranged at a second detection location that differs from the first detection location, with the second detector being configured to register a light component of the light radiated in that has been scattered in the dialysate flow and to produce a second signal which represents the intensity of the registered scattered light component; and comprising an evaluation unit configured to produce a detection signal on the basis of the first signal and the second signal. In particular, the solution according to the invention allows a calibration device for calibrating the brightness of the light source to be dispensed with. This is because possible variations in the brightness of the light source, or of the light radiated in by the latter, that are due to operational reasons are registered equally by means of the first detector and by means of the second detector. This can be accordingly taken into account when producing the detection signal by means of the evaluation unit. As a result, the detection device according to the invention facilitates a simple structure but nevertheless a reliable detection of blood in the dialysate flow since incorrect detections on account of brightness variations of the light source are avoided, while at the same time dispensing with a calibration device. In particular, the light source is configured to carry out step a) of the method according to the invention. The light source is preferably a light-emitting diode. Further preferably, the light source is configured to emit red, green and/or blue light and in this respect is for example a red, green and/or blue light-emitting diode. In particular, the first detector is configured to carry out step b) of the method according to the invention. The first detector is preferably a photodiode. In particular, the second detector is configured to carry out step c) of the method according to the invention. The second detector is preferably a photodiode. The first detector and the second detector are arranged at different locations, specifically at the first detection location and at the second detection location. In this respect, the first detector and the second detector are spaced apart from one another. In particular, the evaluation unit is configured to carry out step d) of the method according to the invention. To avoid repetition, reference is otherwise made to the explanations of the features and the advantages of the method according to the invention. What was stated there is analogously transferable to the setup of the detection device, in particular to the light source, the first detector, the second detector and/or the evaluation unit.

In a further configuration of the invention, the evaluation unit is configured to produce the detection signal on the basis of a change in the first signal over time and a change in the second signal over time. Otherwise, additionally and to avoid repetition, reference is made to the disclosure in the context of the aforementioned embodiment of the method according to the invention, which is analogously transferable to this embodiment of the detection device according to the invention.

In a further embodiment of the invention, provision is made for the light source to be arranged on a first side of a light-transmissive fluid-guiding channel provided for fluid guidance of the dialysate flow along its longitudinal direction, for the first detector to be arranged at a distance from the light source in a radiated-in direction of the light on a second side of the fluid-guiding channel which transversely to the longitudinal direction of the fluid-guiding channel is located opposite the first side, and for the second detector to be arranged on the second side of the fluid-guiding channel and at a distance from the first detector perpendicular to the longitudinal direction of said fluid-guiding channel. The fluid-guiding channel is preferably manufactured from a transparent plastic or from glass. The fluid-guiding channel can in particular be designed as a tube section, as a pipe section, and preferably as a cuvette. Further preferably, the fluid-guiding channel has a circular cross section. Fluid guidance through the fluid-guiding channel is implemented in the longitudinal direction of the fluid-guiding channel. The light source and the first detector are arranged on opposite sides of the fluid-guiding channel, specifically on the first side and the second side, respectively. Preferably, the light source and the first detector are arranged in a common longitudinal center plane and/or transverse center plane of the fluid-guiding channel. In this respect, the radiated-in direction for the light is oriented so as to be transverse to the longitudinal direction of the fluid-guiding channel and hence also transverse to the flow direction of the dialysate flow. A perpendicular orientation, that is to say an orientation of the radiated-in direction at 90° to the longitudinal direction or the flow direction, is preferably provided. The second detector—in relation to an optical axis extending directly between the light source and the first detector and in a line of sight directed perpendicular to a cross section of the fluid-guiding channel—is preferably arranged offset upwardly or downwardly relative to the first detector.

In a further embodiment of the invention, the second detector is arranged so as form an angle of between 5° and 30°, preferably between 18° and 22°, with respect to the radiated-in direction of the light. Said optical axis extending directly between the light source and the first detector extends along the radiated-in direction. In this respect, the second detector is arranged so as to form the above-described angle with respect to the optical axis. An angle of between 5° and 30° facilitates a functional registration of the light component that has been scattered in the dialysate flow. Moreover, the inventors have recognized that an angle of between 18° and 22°, particularly preferably 20°, offers particular advantages for registering the scattered light component.

In a further embodiment of the invention, provision is made for a UV light source to be provided, the latter being also configured to radiate UV light into the dialysate flow and to radiate UV light past the dialysate flow; for the first detector to be configured to register a UV light component of the UV light radiated in that has been transmitted through the dialysate flow and to produce a third signal which represents the intensity of the registered transmitted UV light component; for the second detector to be configured to register the UV light radiated past the dialysate flow and to produce a fourth signal which represents the intensity of the registered UV light radiated past said dialysate flow; and for the evaluation unit to be configured to determine a Kt/V value on the basis of the third signal produced and the fourth signal produced. To avoid repetition, reference is made to the disclosure regarding said embodiment of the method according to the invention, with the features and advantages explained there being analogously transferable to this embodiment of the detection device according to the invention. In particular, the UV light source is configured to carry out step e) of the method. The UV light source is preferably a light-emitting diode. The UV light source is arranged relative to the dialysate flow and/or the fluid-guiding channel in such a way that the emitted UV light is able to be partly radiated into the dialysate flow and partly radiated past the latter. Expressed differently, the UV light source is arranged in such a way that a first optical axis extends between the UV light source and the first detector, and hence the first detection location, through the dialysate flow, and that a second optical axis extends between the UV light source and—away from the dialysate flow and/or the fluid-guiding channel—the second detector, and hence the second detection location. In this embodiment of the invention, the first detector is additionally configured to carry out step f) of the method. In this embodiment of the invention, the second detector is additionally configured to carry out step g) of the method. In this embodiment of the invention, the evaluation unit is additionally configured to carry out step h) of the method. Otherwise, additionally and in order to avoid repetition, reference is made to the disclosure in the context of aforementioned steps e) to h) of the method, which is analogously transferable to the setup of the UV light source, the first detector, the second detector and/or the evaluation unit.

In a further embodiment of the invention, the UV light source is arranged on the first side of the fluid-guiding channel. Preferably, the UV light source is arranged in a common plane with the light source and the first detector and/or the second detector.

In a further embodiment of the invention, a shielding element is provided, by means of which the second detector is shielded from the UV light radiated into the dialysate flow. To avoid repetition, reference is made to the disclosure relating to the embodiment of the method according to the invention, with what has been stated there applying analogously. The shielding element is arranged in such a way that the registration of the scattered light component of the radiated-in light and the registration of the UV light radiated past the dialysate flow, respectively by means of the second detector, is not impaired by the shielding element. The shielding element is opaque, at least for the wavelength of the emitted UV light. Preferably, the shielding element is substantially completely opaque.

In a further embodiment of the invention, a control unit is provided and configured to drive the light source and the UV light source alternately, preferably with an alternation frequency of 1 kHz. As a result of alternate driving, the light and the UV light are emitted alternately over time, and hence in intermittent fashion in each case, and therefore also accordingly registered alternately by means of the first detector and the second detector. The control unit may be a separate unit of the detection device or may be integrated into a single unit together with the evaluation unit.

In a further embodiment of the invention, a housing is provided, in which at least the light source, the first detector and the second detector are received. This embodiment of the invention simplifies assembly and servicing of the detection device in particular, since the components received in the housing can easily be assembled on the dialysis machine together by handling the housing and/or can be removed from said dialysis machine together.

In a further embodiment of the invention, the UV light source and/or the shielding element are received within the housing. This is a particularly preferred embodiment of the invention since it is possible to dispense with an additional housing for receiving the UV light source and/or the shielding element. Instead, the components, in particular the optical elements, required for the blood leakage detection and for the Kt/V value determination can be received together in the housing.

The invention moreover relates to a dialysis machine comprising a dialyzer and a detection device according to the description above arranged on the outlet side of the dialyzer.

BRIEF DESCRIPTION OF THE DRAWING FIGURES

Further advantages and features arise from the following description of preferred exemplary embodiments of the invention, which are illustrated on the basis of the drawings.

DETAILED DESCRIPTION

Figure 1:
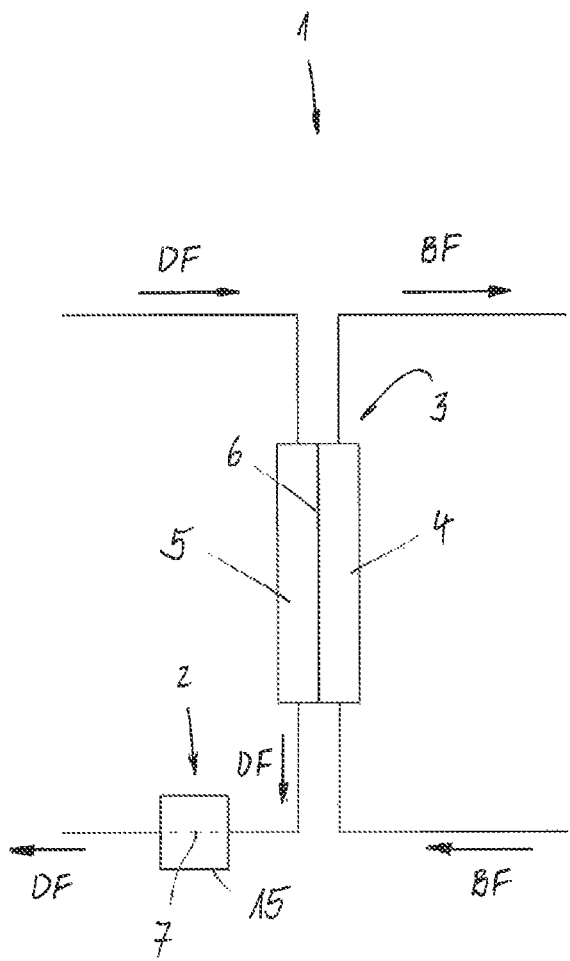
FIG. 1 shows a schematic illustration of a section of an embodiment of a dialysis machine according to the invention, which is provided with an embodiment of a detection device according to the invention.

FIG. 1 schematically shows a detail of an embodiment of a dialysis machine 1 according to the invention, which is provided with an embodiment of a detection device 2 according to the invention. The dialysis machine 1 is provided for extracorporeal blood treatment and comprises a dialyzer 3 having a blood chamber 4 and a dialysate chamber 5. The blood chamber 4 is separated from the dialysate chamber 5 by means of a semipermeable membrane 6 and is connected to an extracorporeal blood circuit, not denoted in any more detail, in fluid-guiding fashion, blood to be treated being conveyed in said blood circuit through the blood chamber 4 along a flow direction BF. The dialysate chamber 5 is connected to a dialysate circuit, not denoted in any more detail, in which dialysate D (FIG. 2), which may also be referred to as dialysis fluid, is conveyed through the dialysate chamber 5 along a flow direction DF while forming a dialysate flow DS in the process.

Figure 2:
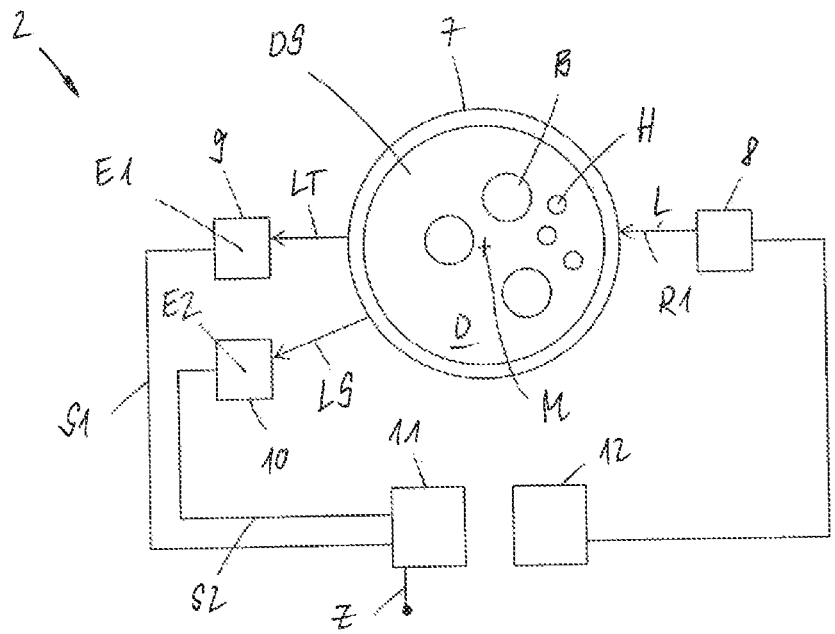
FIG. 2 shows a schematically much simplified representation of the detection device according to FIG. 1, with the latter being configured to carry out an embodiment of the method according to the invention.

During the extracorporeal blood treatment, substances usually eliminated with urine pass via the semipermeable membrane 6 from the blood conveyed through the blood chamber 4 to the dialysate flow DS conveyed through the dialysate chamber 5. These substances usually eliminated with urine comprise in particular urea H, which for graphical clarification on the basis of FIG. 2 is represented in schematically much simplified fashion in particle or droplet shape in the dialysate flow DS. In a functional state of the semipermeable membrane 6, the blood is sealed in fluid-tight fashion in the blood chamber 4 vis-à-vis the dialysate chamber 5. In the case of a rupture of the semipermeable membrane 6 due to failure, blood leaks from the blood chamber 4 into the dialysis chamber 5 via the rupture, and hence into the dialysate flow DS. For graphical clarification, blood B that has leaked into the dialysate flow DS in this manner is represented in schematically much simplified fashion in particle or droplet shape. Such blood leakage can lead to serious medical complications in the patient to be treated and to technical impairments of the dialysis machine 1.

The detection device 2 serves to detect the blood B that has leaked into the dialysate flow DS. For this purpose, the detection device 2 is arranged on the outlet side of the dialysate chamber 5 in the flow direction DF and the dialysate flow DS flows through said detection device when in the operational mounted state. A fluid-guiding channel 7 is provided at least in the region of the detection device 2 for the purposes of fluid guidance of the dialysate flow DS. In the embodiment shown, the fluid-guidance channel 7 is formed as a section of the machine-side dialysate circuit and, in this respect, not as a constituent part of the detection device 2. In an embodiment that is not shown, the fluid-guiding channel instead is a component of the detection device, which on the inlet side and the outlet side of the detection device is in each case connected in fluid-guiding fashion to the machine-side dialysate circuit.

As shown on the basis of FIG. 2, the detection device 2 comprises a light source 8, a first detector 9, a second detector 10 and an evaluation unit 11.

The light source 8 is configured to radiate light L into the dialysate flow DS. The first detector 9 is arranged at a first detection location E1 which on the basis of FIG. 2 has been plotted in simplified fashion in the center of the schematic representation of the first detector 9. The first detector 9 is configured to register a light component LT of the radiated-in light L that has been transmitted through the dialysate flow DS and to produce a first signal S1. In this case, the first signal S1 represents the intensity of the registered transmitted light component LT. The second detector 10 is arranged at a second detection location E2, which is arranged at a distance from the first detection location E1 in a manner yet to be described in more detail. In this case, the second detector 10 is configured to register a light component LS of the radiated-in light L that has been scattered in the dialysate flow DS and to produce a second signal S2. The second signal S2 represents the intensity of the registered scattered light component LS. The evaluation unit 11 is configured to produce a detection signal Z on the basis of the first signal S1 and the second signal S2. More precisely, the evaluation unit 11 in the embodiment shown is configured to produce the detection signal Z on the basis of a change in the first signal S1 over time and a change in the second signal S2 over time that will be explained in more detail on the basis of FIG. 4.

To detect blood B that has leaked into the dialysate flow DS in the manner described above, the light L is radiated into the dialysate flow DS through the light-transmissive fluid-guiding channel 7 by means of the light source 8. In the dialysate flow DS, the radiated-in light L is partly scattered at the blood B situated in the dialysate flow DS and partly absorbed by said blood. The transmitted light component LT arising in this case is registered at the first detection location E1 by means of the first detector 9 and converted into the first signal S1. The scattered light component LS arising in this case is registered at the second detection location E2 by means of the second detector 10 and converted into the second signal S2. The signals S1, S2 are processed by means of the evaluation unit 11 which for this purpose is connected via signal lines, not denoted in any more detail, to both the first detector 9 and the second detector 10. In the embodiment shown, the detection signal Z is produced when the changes in the signals S1, S2 over time are in the opposite sense to one another. This is clarified below on the basis of FIG. 4.

Figure 4:
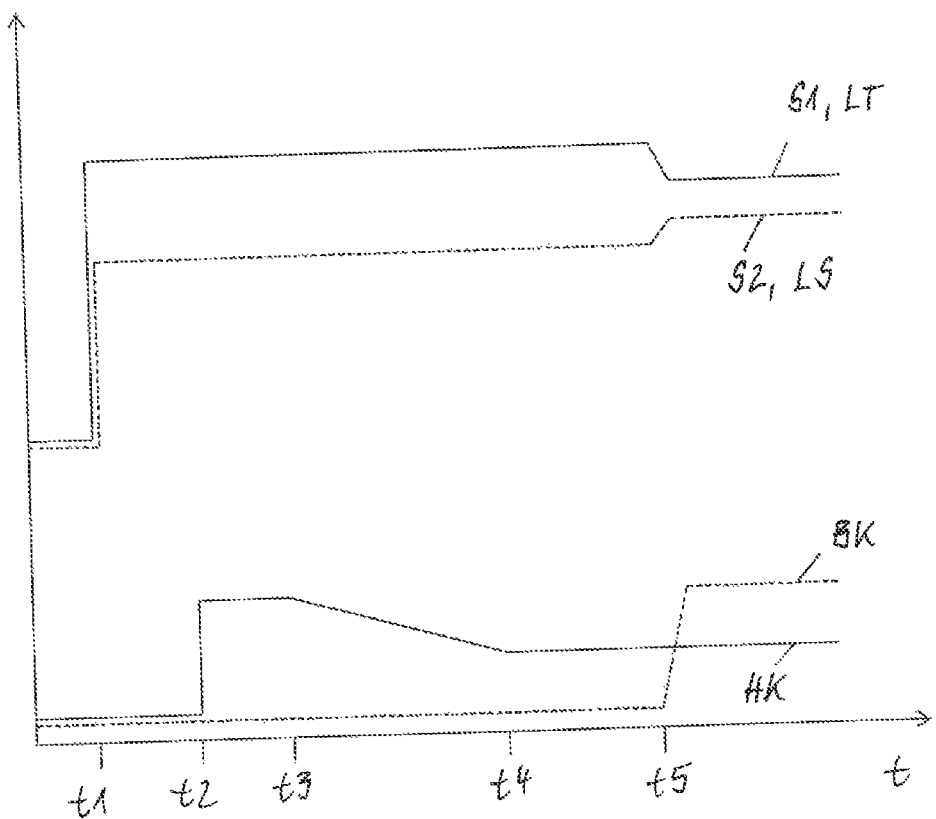
FIG. 4 shows a schematic diagram for further clarification of the functionality of the detection device according to FIG. 2 and of the method able to be carried out with the latter.

FIG. 4 shows the first signal S1 and the second signal S2 over time t for an exemplary course of the extracorporeal blood treatment by means of the dialysis machine 1. As explained above, the curves of the signals S1, S2 shown in exemplary fashion represent the registered transmitted light component LT and the registered scattered light component LS, respectively, and so the curves thereof are plotted congruently with those of the signals S1, S2. Moreover, the diagram according to FIG. 4 shows the time curve of a blood concentration BK of the blood B and a urea concentration HK of the urea H in the dialysate flow DS over time t.

Between times t1 and t2, the exemplary extracorporeal blood treatment provides for what is known as priming, i.e., venting, of the dialysate circuit. In the process, the dialysate circuit is filled with the dialysate D, with air being flushed out of the fluid-guiding channel 7 in particular and being replaced by dialysate D. As a consequence of the different optical properties of air and dialysate D, there naturally is a change in the transmitted and scattered light components LT and LS, respectively. These rise at the time t1. A corresponding statement applies to the signals S1, S2.

The actual blood treatment starts at the time t2, at which point substances usually eliminated with urine, in particular the urea H, pass via the semipermeable membrane 6 from the blood chamber 4 into the dialysate flow DS. Accordingly, the urea concentration HK increases at the time t2.

The increasing urea concentration HK does not bring about a change in the transmitted light component LT and/or in the scattered light component LS.

The urea concentration HK remains unchanged until the time t3. Then, there is a decrease in the urea concentration HK, which continues up to the time t4. This change in the urea concentration HK over time also exhibits no effect on the signals S1, S2 and/or the light components LT, LS. That is to say, the light component LT and hence also the first signal S1 remain untouched thereby. The light component LS and hence the second signal S2 also remain untouched thereby.

There is no further change in the urea concentration HK after the time t4.

At the time t5 there is a rupture in the semipermeable membrane 6, and so blood passes from the blood chamber 4 into the dialysate chamber 5 and hence into the dialysate flow DS. This leads to an increase in the blood concentration BK. The increasing blood concentration BK leads to increased scattering of the radiated-in light L at the blood B that has leaked in (FIG. 2). Accordingly, the scattered light component LS increases at the time t5. As a result of this increase in the scattered light component LS, there is a corresponding change in the second signal S2 over time. At the same time, there is an opposite change in the transmitted light component LT over time, and hence also in the first signal S1 over time.

The above-described change in the light components LT, LS, and hence also in the first signal S1 and the second signal S2, which change is in the opposite sense over time, is a clear indicator of the blood leakage BK occurring at the time t5. Accordingly, the detection signal Z is output by means of the evaluation unit 11 when such an above-described opposite change in the signals S1, S2 over time is present.

In the present embodiment, the detection signal Z is an acoustic and/or optical warning signal that is perceivable by a user of the dialysis machine 1. In an embodiment that is not shown, the detection signal Z is a control signal for controlling at least one function of the dialysis machine 1. By way of example, the dialysis machine 1 can be controlled by the detection signal Z to abort the extracorporeal blood treatment, which involves interrupting the conveyance of the blood within the blood circuit and/or the conveyance of the dialysate D in the dialysate circuit.

Incidentally, it is understood that the rupture occurring at time t5 in exemplary fashion in the present case may instead of course occur at any other times during the extracorporeal blood treatment, for example prior to time t4.

In the embodiment shown, the light source 8 is arranged on a first side, not denoted in any more detail, of the light-transmissive fluid-guiding channel 7. Both the first detector 9 and the second detector 10 are arranged on a second side of the fluid-guiding channel 7 which is opposite the first side and hence also opposite the light source 8 transversely, to be more precise perpendicularly, to the flow direction DF of the dialysate flow DS. In relation to the plane of the drawing of FIG. 2, the flow direction DF is oriented projecting perpendicularly out of the image plane. Expressed differently, the first detector 9 is arranged at a distance from the light source 8 along a radiated-in direction R1 of the light L.

In the present embodiment, the light source 8 and the first detector 9 are each arranged level with a transverse center axis of the fluid-guiding channel 7, which is not denoted in any more detail. An imaginary optical axis between the light source 8 and the first detector 9 and hence also the first detection location E1 is therefore aligned coaxially with the transverse center axis of the fluid-guiding channel 7.

In the present case, the second detector 10 is arranged offset in relation to the transverse center axis of the fluid-guiding channel 7. In this case, the second detector is arranged so as to form an angle, not denoted in any more detail, with respect to the radiated-in direction R1 of the light L. Expressed differently, the second detector 10 is positioned at an angle, which is specified in more detail, with respect to a center M of the fluid-guiding channel 7. Unlike what is to be expected from FIG. 2, the angle with respect to the radiated-in direction R1 and hence also with respect to the transverse center axis of the fluid-guiding channel 7 is 20° in the present case.

In the embodiment shown, the light source 8, the first detector 9 and the second detector 10 are arranged in a common plane.

In the embodiment according to FIG. 2, the light source 8 is a light-emitting diode. To drive the latter, a control device 12 is provided in the present case. The light source 8 is drivable by means of the control device 12 to emit the light L continuously over time and/or at discrete time intervals, i.e., intermittently. The first detector 9 and the second detector 10 are a photodiode in each case. The evaluation unit 11 and the control unit 12 may—as indicated schematically in FIG. 2—be provided as structurally and/or functionally separate units. In an embodiment that is not shown, the evaluation unit and the control unit are integrated in a common unit.

Figure 3:
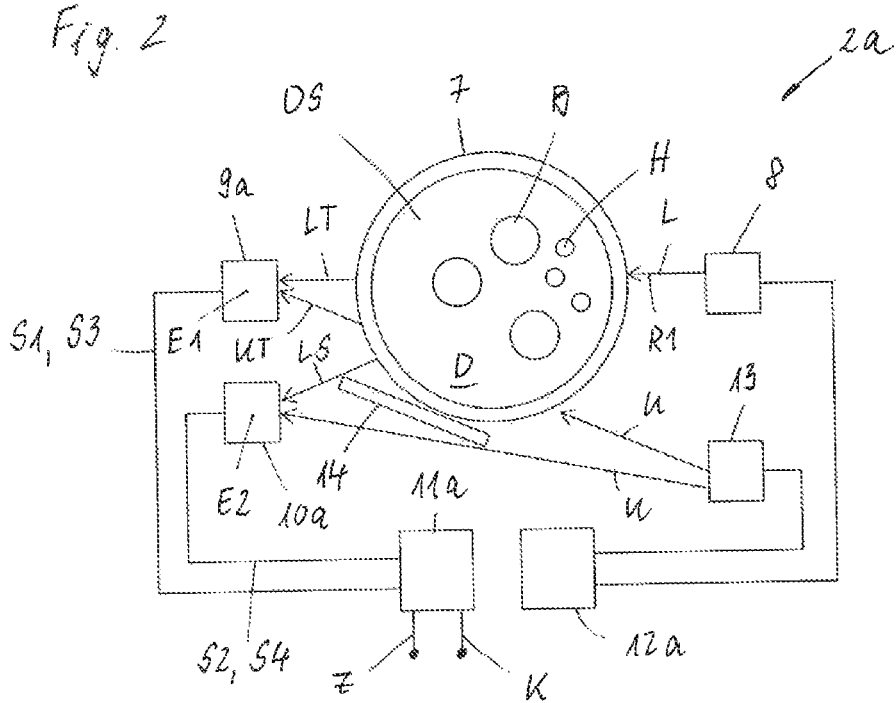
FIG. 3 shows, in a representation corresponding to FIG. 2, a further embodiment of a detection device according to the invention, with the latter being configured to carry out a further embodiment of the method according to the invention.

The detection device 2a according to FIG. 3 has a structure that largely corresponds to that of the detection device 2 according to FIG. 2. To avoid repetition, reference is made to the disclosure in this respect in connection with the detection device 2 according to FIG. 2, which analogously also applies with regard to the detection device 2a. Only the essential differences of the detection device 2a are discussed below. On account of these differences, the detection device 2a is configured to carry out the method for detecting blood and urea in the dialysate flow DS, which is schematically clarified on the basis of FIGS. 5 and 7.

The detection device 2a essentially differs from the detection device 2 in that a UV light source 13 is provided. The UV light source 13 is configured to radiate UV light U into the dialysate flow DS and to radiate UV light U past the dialysate flow DS. The first detector 9a is configured in a manner corresponding to the first detector 9 of the detection device 2 according to FIG. 2. Additionally, the first detector 9a is configured to register a UV light component UT of the radiated-in UV light U that has been transmitted through the dialysate flow DS and to produce a third signal S3. The third signal S3 represents the intensity of the registered transmitted UV light component UT. The second detector 10a is configured in a manner corresponding to the second detector 10 of the detection device 2 according to FIG. 2. Additionally, the second detector 10a is configured to register the UV light U that has been radiated past the dialysate flow DS and to produce a fourth signal S4. The fourth signal S4 represents the intensity of the registered UV light U that has been radiated past said dialysate flow. The evaluation unit 11a is configured in accordance with the evaluation unit 11 of the detection device 2 according to FIG. 2. Additionally, the evaluation unit 11a is configured to determine a Kt/V value K on the basis of the third signal S3 produced and the fourth signal S4 produced.

The Kt/V value K is a variable known per se in the field of dialysis technology and allows conclusions to be drawn about the progress of the extracorporeal blood treatment. It is known that the Kt/V value K is determined on the basis of the urea concentration HK of the urea H in the dialysate flow DS. It is known that the urea concentration HK is approximately linearly related to the absorption of the UV light U radiated into the dialysate flow DS. Accordingly, the transmitted UV light component UT changes depending on the urea concentration HK. Such a change is registered by means of the first detector 9a and converted into the third signal S3. In this case, the registration of the UV light U radiated past the dialysate flow DS by means of the second detector 10a and the conversion thereof into the fourth signal S4 serves as a reference. The evaluation operations to be carried out by means of the evaluation unit 11a for determining the Kt/V value K on the basis of the third signal S3 and the fourth signal S4 are in principle known as such, and so further explanations in this respect can be omitted.

Figure 5:
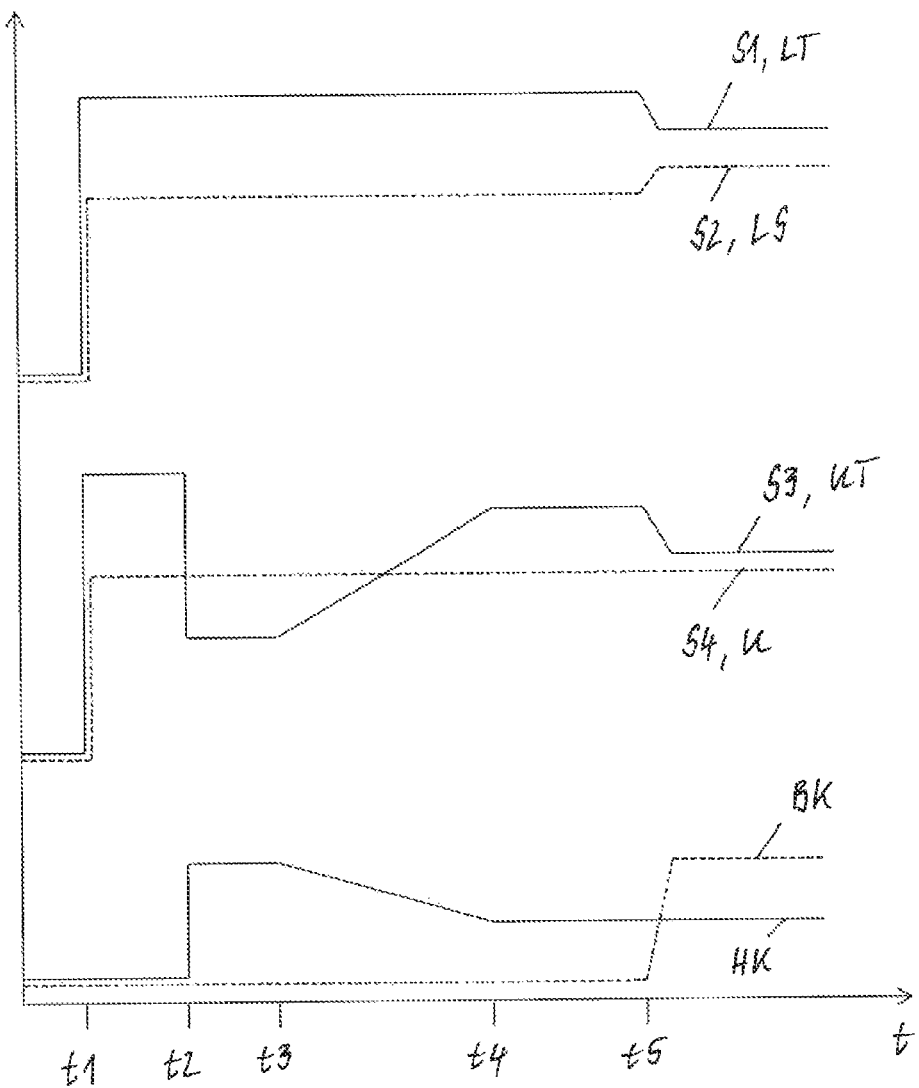
FIG. 5 shows a further schematic diagram for clarification of the functionality of the detection device according to FIG. 3 and of the method able to be carried out with the latter.

In a manner corresponding to FIG. 4, FIG. 5 shows an exemplary course of the extracorporeal blood treatment by means of the dialysis machine 1 over time t, using the detection device 2a. In this case, the exemplary curves shown there for the signals S1, S2 or the corresponding curves of the transmitted light component LT and the detected scattered light component LS correspond to the curves already explained on the basis of FIG. 4. A corresponding statement applies in respect of the urea concentration HK and the blood concentration BK. To avoid repetition, reference is therefore made to the explanations in this respect which were provided in connection with FIG. 4.

FIG. 5 additionally shows the third signal S3 and the fourth signal S4 over time. As explained above, the curves of the signals S3, S4, shown in exemplary fashion, represent the intensity of the registered transmitted UV light component UT and the intensity of the registered UV light U that has been radiated past said dialysate flow, respectively.

As the urea concentration HK increases at time t2, there is an increased attenuation of the UV light radiated into the dialysate flow DS, and so the transmitted UV light component UT falls, as does accordingly the third signal S3. The intensity of the captured UV light U radiated past said dialysate flow and hence also the fourth signal S4 remain untouched thereby.

With the decrease in the urea concentration HK starting at the time t3, there is an increase in the transmitted UV light component UT and hence also an increase in the third signal S3. This lasts up to the time t4. The urea concentration HK remains unchanged after the time t4.

On account of the blood leakage occurring at the time t5, there is moreover a decrease in the transmitted UV light component UT and hence also a decrease in the third signal S3. This change in the third signal S3 shows no practical effect on the determination of the Kt/V value K, since the extracorporeal blood treatment is interrupted in any case following the detection of the blood leakage that occurs at the time t5.

In the embodiment shown, the UV light source 13 is arranged in a common plane with the first detector 9a and the second detector 10a. Consequently, all optical components 8, 9a, 10a, 13 are located in a common plane in the present case. The UV light source 13 is arranged with a downward offset relative to the fluid-guiding channel 7 and the light source 8 so that there can be a direct emission of the UV light from the UV light source 13 in the direction of the second detection location E2 and hence also in the direction of the second detector 10a. In this respect, this emission takes place past the fluid-guiding channel 7.

The detection device 2a moreover comprises a shielding element 14 which is arranged relative to the fluid-guiding channel 7, the UV light source 13 and/or the second detector 10a in such a way that the latter is shielded by means of the shielding element 14 from light components of the radiated-in UV light U that have been scattered in the dialysate flow DS or otherwise deflected in the direction of the second detection location E2. At the same time, the shielding element 14 is arranged in such a way that the light component LS of the radiated-in light L that has been scattered in the dialysate flow DS is able to be registered by means of the second detector 10a.

The control device 12a is configured for alternate driving of the light source 8 and the UV light source 13 in the embodiment according to FIG. 3. Driving is preferably implemented with an alternation frequency of 1 kHz. Expressed differently, the light L and the UV light U are radiated alternately over time into the dialysate flow DS and are accordingly converted alternately over time into the signals S1, S2 and S3, S4 by means of the first detector 9a and the second detector 10a. In the case of a sufficiently high alternation frequency there is, from a practical point of view, virtually simultaneous production of the detection signal Z and determination of the Kt/V value K.

As is further shown on the basis of FIG. 1, a housing 15 is provided. In the embodiment according to FIG. 2, the housing 15 receives at least the light source 8, the first detector 9 and the second detector 10. Additionally, the evaluation unit 11 and the control unit 12 may be received in the housing 15.

A corresponding statement applies with regard to the embodiment according to FIG. 3, and so a housing for receiving substantially all components of the detection device 2a can also be provided in that case.

Figures 6, 7:
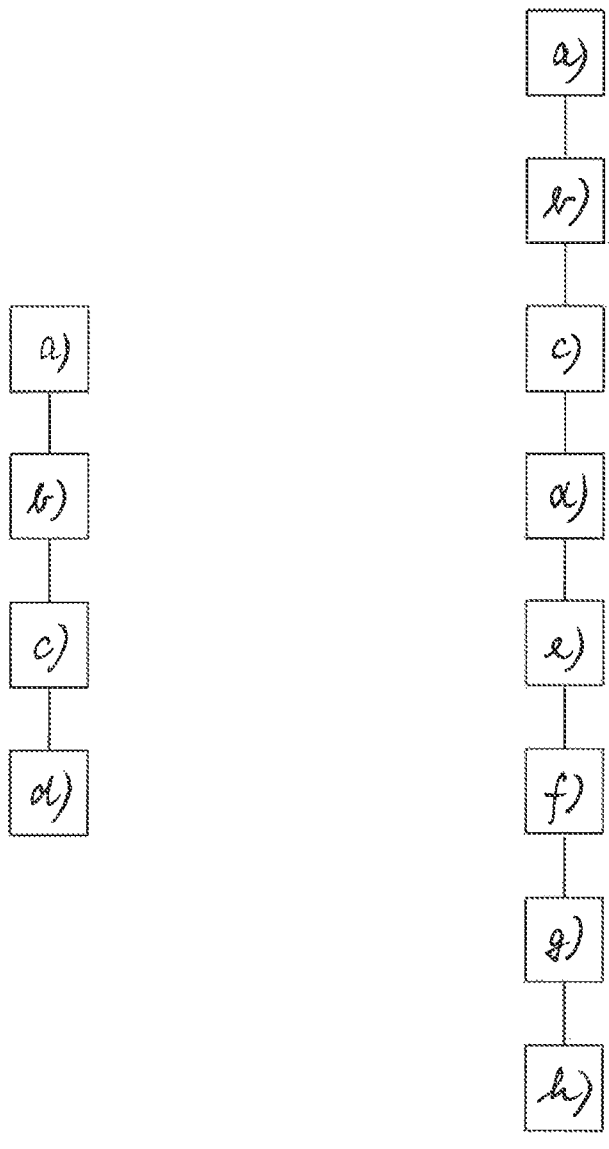
FIG. 6 shows a schematic flowchart for further clarification of the method able to be carried out with the detection device according to FIG. 2.
FIG. 7 shows a schematic flowchart for clarification of the method able to be carried out with the detection device according to FIG. 3.

FIG. 6 shows a schematically much simplified flowchart representation of the method for detecting blood comprising steps a) to d), which is able to be carried out by means of the detection device 2 according to FIG. 2. FIG. 7 shows a schematically much simplified flowchart of the method for detecting blood and urea comprising steps a) to h), which is able to be carried out by means of the detection device 2a according to FIG. 3.

The invention claimed is:

1. A method for detecting blood in a dialysate flow of a dialysis machine during an extracorporeal blood treatment, the method comprising the following steps:
   a) radiating light into the dialysate flow;
   b) registering, at a first detection location, a first light component of the light radiated in that has been transmitted through the dialysate flow and producing a first signal which represents a first intensity of the first light component;
   c) registering, at a second detection location, a second light component of the light radiated in that has been scattered in the dialysate flow and producing a second signal which represents a second intensity of the second light component;
   d) producing a detection signal based on the first signal and the second signal;
   e) emitting UV light, with the UV light being radiated into the dialysate flow and being radiated past the dialysate flow;
   f) registering, at the first detection location, a UV light component of the UV light radiated in that has been transmitted through the dialysate flow and producing a third signal which represents a third intensity of the UV light component;
   g) registering, at the second detection location, the UV light radiated past the dialysate flow and producing a fourth signal which represents a fourth intensity of the UV light radiated past said dialysate flow; and h) determining a Kt/V value based on the third signal and the fourth signal.

2. The method as according to claim 1, wherein the detection signal is produced when a change in the first signal over time is in an opposite sense to a change in the second signal over time.

3. The method according to claim 1, wherein the second detection location is shielded from the UV light radiated into the dialysate flow.

4. The method according to claim 1, wherein the light and the UV light are radiated into the dialysate flow in alternating fashion, with the first signal and the third signal being produced alternately by a first detector arranged at the first detection location and with the second signal and the fourth signal being produced alternately by a second detector arranged at the second detection location.

5. A detection device for carrying out a method according to claim 1,
the detection device comprising:
at least one light source configured to radiate light into the dialysate flow;
a first detector arranged at the first detection location, with the first detector being configured to register the first light component of the light radiated in that has been transmitted through the dialysate flow and to produce the first signal which represents the first intensity of the first light component;
a second detector arranged at the second detection location that differs from the first detection location, with the second detector being configured to register the second light component of the light radiated in that has been scattered in the dialysate flow and to produce the second signal which represents the second intensity of the second light component;
an evaluation unit configured to produce a detection signal based on the first signal and the second signal; and
comprising a UV light source configured to radiate the UV light into the dialysate flow and to radiate the UV light past the dialysate flow;
the first detector being configured to register the UV light component of the UV light radiated in that has been transmitted through the dialysate flow and to produce the third signal which represents the third intensity of the UV light component;
the second detector being configured to register the UV light radiated past the dialysate flow and to produce the fourth signal which represents the fourth intensity of the registered UV light radiated past said dialysate flow; and
the evaluation unit being configured to determine a Kt/V value based on the third signal and the fourth signal.

6. The detection device according to claim 5, wherein the evaluation unit is configured to produce the detection signal based on a change in the first signal over time and a change in the second signal over time.

7. The detection device according to claim 5 wherein the at least one light source is arranged on a first side of a light-transmissive fluid-guiding channel provided for fluid guidance of the dialysate flow along its longitudinal direction, in that the first detector is arranged at a distance from the at least one light source in a radiated-in direction of the light on a second side of the fluid-guiding channel which transversely to the longitudinal direction of the fluid-guiding channel is located opposite the first side, and in that the second detector is arranged on the second side of the fluid-guiding channel and at a distance from the first detector perpendicular to the longitudinal direction of said fluid-guiding channel.

8. The detection device according to claim 7, wherein the second detector is arranged so as form an angle of between 5° and 30° with respect to a radiated-in direction of the at least one light source.

9. The detection device according to claim 5, wherein the UV light source is arranged on the first side of the fluid-guiding channel.

10. The detection device according to claim 5, further comprising a shielding element that shields the second detector from the UV light radiated into the dialysate flow.

11. The detection device according to claim 5, further comprising a control unit configured to drive the at least one light source and the UV light source alternately.

12. The detection device according to any claim 5, further comprising a housing that receives the at least one light source, the first detector and the second detector.

13. The detection device according to claim 12, wherein the UV light source and/or the shielding element is/are received within the housing.

14. A dialysis machine comprising:
a detection device according to claim 5; and
a dialyzer,
wherein the detection device is arranged on the outlet side of the dialyzer.

* * * * *